US011439691B2

(12) United States Patent
Fuhrherr et al.

(10) Patent No.: US 11,439,691 B2
(45) Date of Patent: Sep. 13, 2022

(54) AQUEOUS SOLUTION OF BURLULIPASE COMPRISING CALCIUMIONS

(71) Applicant: Nordmark Pharma GmbH, Uetersen (DE)

(72) Inventors: Richard Fuhrherr, Uetersen (DE); Annika Müller-Lucks, Uetersen (DE); Katharina Rützel, Uetersen (DE); Jan Lüdemann, Uetersen (DE); Martin Werner, Uetersen (DE)

(73) Assignee: NORDMARK PHARMA GMBH, Uetersen (DE)

( * ) Notice: Subject to any disclaimer, the term of this patent is extended or adjusted under 35 U.S.C. 154(b) by 0 days.

(21) Appl. No.: 16/490,550

(22) PCT Filed: Mar. 5, 2018

(86) PCT No.: PCT/EP2018/055380
§ 371 (c)(1),
(2) Date: Sep. 1, 2019

(87) PCT Pub. No.: WO2018/158467
PCT Pub. Date: Sep. 7, 2018

(65) Prior Publication Data
US 2020/0009233 A1   Jan. 9, 2020

(30) Foreign Application Priority Data

Mar. 3, 2017 (DE) .......................... 102017104480.9

(51) Int. Cl.
| | |
|---|---|
| *A61K 38/46* | (2006.01) |
| *A61K 9/08* | (2006.01) |
| *A61K 47/02* | (2006.01) |
| *C12N 9/18* | (2006.01) |
| *C12N 9/96* | (2006.01) |

(52) U.S. Cl.
CPC ............. *A61K 38/465* (2013.01); *A61K 9/08* (2013.01); *A61K 47/02* (2013.01); *C12N 9/18* (2013.01); *C12N 9/96* (2013.01); *C12Y 301/01003* (2013.01)

(58) Field of Classification Search
CPC .............................................. C12Y 301/01003
See application file for complete search history.

(56) References Cited

U.S. PATENT DOCUMENTS

| | | | |
|---|---|---|---|
| 4,959,179 A | 9/1990 | Aronson et al. | |
| 5,645,832 A | 7/1997 | Braatz et al. | |
| 5,968,792 A * | 10/1999 | Wenzel ................. | C12P 7/6418 |
| | | | 435/134 |
| 2010/0308056 A1 | 12/2010 | Brandenburger et al. | |
| 2011/0293590 A1 | 12/2011 | Rämsch et al. | |
| 2013/0015204 A1 | 1/2013 | Gol | |

FOREIGN PATENT DOCUMENTS

| | | |
|---|---|---|
| CN | 102231988 A | 11/2011 |
| CN | 103981168 A | 8/2014 |
| DE | 102009006594 A1 | 8/2010 |
| DE | 202014007438 U1 | 12/2014 |
| EP | 0592478 B1 | 6/1992 |
| EP | 3090638 A1 | 12/1998 |
| EP | 2535401 A1 | 12/2012 |
| EP | 2391382 B1 | 6/2014 |
| EP | 3090638 A1 | 11/2016 |
| JP | H08500013 A | 1/1996 |
| JP | 2002369681 A | 12/2002 |
| JP | 2012516289 A | 7/2012 |
| JP | 2015071458 A | 4/2015 |
| JP | 2015212283 A | 11/2015 |
| WO | 9403592 A1 | 2/1994 |
| WO | 2004013123 A1 | 2/2004 |
| WO | 2010085975 A1 | 8/2010 |
| WO | 2011080267 A2 | 7/2011 |
| WO | 2013076232 A1 | 5/2013 |
| WO | 2013171241 A1 | 11/2013 |
| WO | 2015078742 A1 | 6/2015 |
| WO | 2016115286 A1 | 7/2016 |

OTHER PUBLICATIONS

Rathi et al., Process Biochemistry, 2001, 37:187-192.*
Khattabi et al., JBC, 2000, 275(35):26885-26891.*
International Search Report and Written Opinion for PCT/EP2018/055380, dated Sep. 7, 2018.
English translation of the Written Opinion for PCT/EP2018/055380, dated Sep. 7, 2018.
Structure of a new 6-deoxy-α-D-talan from Burkholderia (Pseudomonas) plantarii strain DSM 6535, Carbohydrate Research, 1997, vol. 300, pp. 143-151.
English translation of Office Action for Japanese Pat. App. No. 2019-547690, dated Jan. 28, 2020.
English translation of search report for German Pat. App. No. 10 2017 104 480.9, dated Jun. 29, 2017.
Sharma Rohit et al., Production, purification, characterization, and applications of lipases, (2001) Biotechnology Advances vol. 19, pp. 627-662.
Kimura, H. et al., "Activation of Human Pancreatic Lipase Activity by Calcium and Bile Salts", J. Biochem. 92, 243-251 (1982).

(Continued)

*Primary Examiner* — Bin Shen
(74) *Attorney, Agent, or Firm* — Grogan, Tuccillo & Vanderleeden LLP

(57) ABSTRACT

The present invention relates to an aqueous solution comprising burlulipase which is characterized in that it contains calcium ions. In particular, it also relates to corresponding pharmaceuticals. Such pharmaceuticals are suitable for the treatment of exocrine pancreatic insufficiency. These pharmaceuticals are particularly suitable for treating patients having cystic fibrosis and in pediatrics. Another aspect of the present invention relates to container-packaged solutions and pharmaceuticals as mentioned above, which are containers produced by the blow-fill-seal method, and to methods for producing such packaged solutions and pharmaceuticals.

26 Claims, No Drawings

(56) References Cited

OTHER PUBLICATIONS

Saboury, A. A. et al., "Effect of calcium binding on the structure and stability of human growth hormone", International Journal of Biological Macromolecules 36 (2005) 305-309.
Decision to Grant a Patent (Communication under Rule 71(3)) for corresponding European Patent App. No. 18711043.2, dated Jul. 18, 2019.
Corresponding Chinese Application No. 2018800252776 Office Action dated Jul. 23, 2020 with English Translation.
Corresponding Japanese Application No. 2019-547690 Office Action dated Jan. 20, 2020 with English Translation.
Zahringer, et al.; Carbohydrate Research; 300 (1997) 143-151; Structure of a new 6-deoxy-a-d-talan from Burkholderia (Pseudomonas) plantarii strain DSM 6535, which is different from the O-chain of the lipopolysaccharide.

* cited by examiner

AQUEOUS SOLUTION OF BURLULIPASE COMPRISING CALCIUMIONS

INTRODUCTION

The present invention relates to an aqueous solution comprising burlulipase, which is characterized in that it contains calcium ions. In particular, it also relates to corresponding pharmaceutical products. Such pharmaceutical products are suitable for the treatment of exocrine pancreatic insufficiency. These pharmaceutical products are particularly suitable for the treatment of patients having mucoviscidosis and in pediatrics. A further aspect of the present invention relates to solutions and pharmaceutical products, as mentioned above, packaged in containers, which are containers produced by means of the blow-fill-seal process, and to methods for producing such packaged solutions and pharmaceutical products.

PRIOR ART

Exocrine pancreatic insufficiency is a disease, in which the pancreas does not provide any digestive enzymes or not in sufficient quantities. For treatment, an enzyme substitution has long been used, in which a product obtained from the pancreases of pigs is administered in the form of so-called "pancreatin". This is a solid produced in a multi-stage process, which comprises the degreasing of pancreases from pigs and the removal of fibers therefrom. Pancreatin is a brown powder, which, in addition to the desired main constituents lipase, protease and amylase, also contains a large number of residues from the pancreases of the pigs. This treatment is very successful and usually without serious side effects. However, it has two disadvantages. On the one hand, large quantities (large masses) of pancreatin must be taken, which impairs compliance. On the other hand, the pancreatin contains varying amounts of impurities, which also depend on the raw material. In particular, pancreatin contains residual quantities of viral and microbial impurities originating from the raw material. In view of the discussion about bovine spongiform encephalopathy, biological impurities originating from mammals in pharmaceutical products are seen increasingly critical by the approval authorities. Therefore, approvals of pharmaceutical products produced from animal or human tissue are increasingly problematic. Furthermore, pancreatin cannot be administered in a liquid form, which represents an obstacle for use in pediatrics.

EP 2 391 382 B1 describes pharmaceutical preparations containing bacterial lipases in aqueous solutions. These are suitable for the treatment of pancreatic insufficiency, in particular in mucoviscidosis, and for the treatment of children as well as for the treatment of pancreatitis. Among other things, the enzyme burlulipase was obtained from *Burkholderia plantarii* (triacylglycerol lipase; EC-3.1.1.3) by expression, and its suitability for enzyme substitution in exocrine pancreatic insufficiency has been verified. Burlulipase is suitable for the therapy of exocrine pancreatic insufficiency, but can only be stored and administered under certain conditions. In particular, solutions of burlulipase can only be stored for a prolonged period of time in a refrigerated form without reduction of its activity. Therefore, it is difficult to provide solutions of burlulipase for the treatment of exocrine pancreatic insufficiency, which are long-term stable at room temperature and therefore can be stored at room temperature.

It is known that various reagents, such as buffer systems, sugars, metal ions, emulsifiers, etc. can influence the stability of proteins and in particular of enzymes. For pancreatic lipase, an influence of calcium ions on the activity was verified (see Kimura, H. et al., "Activation of Human Pancreatic Lipase Activity by Calcium and Bile Salts", *J. Biochem.* 92, 243-251 (1982)), and for the human growth hormone, an influence of calcium ions on stability was verified (see Saboury, A. A. et al., "Effect of calcium binding on the structure and stability of human growth hormone", International Journal of Biological Macromolecules 36 (2005) 305-309).

In the article by Ahmed M. K. Youssef and Gerhard Winter, "A critical evaluation of microcalorimetry as a predictive tool for long term stability of liquid protein formulations: Granulocyte Colony Stimulating Factor (GCSF)", *European Journal of Pharmaceutics and Biopharmaceutics* 84 (2013), pages 145 to 155, micro-differential scanning calorimetry (dynamic micro-differential calorimetry) is established as a method for determining changes in the tertiary structure of proteins, in particular enzymes, in solutions. Therefore, this method is suitable for determining the stability of enzymes in solutions. For this reason, this analytical method is used in the present application. Hereinafter, micro-differential scanning calorimetry is also referred to as microcalorimetry or abbreviated by μDSC.

OBJECT OF THE PRESENT INVENTION

It was an object of the present invention to provide solutions of burlulipase which have an increased thermal stability compared to solutions of burlulipase in pure water. In particular, the solutions should have a higher storage capability at temperatures of more than 10° C., and particularly preferably, the solutions should have a higher storage capability at 15 to 35° C. In particular, it is also an object of the present invention to provide burlulipase preparations which have sufficient thermal stability, which allows them to be taken even after sequential storage. A further object of the present invention is to provide preparations of burlulipase, which can be produced as easily as possible and are as sterile as possible and which can be precisely dosed and can be easily taken.

DESCRIPTION OF THE INVENTION

The International Nonproprietary Name (INN) as a name for a medicinal active substance in the public domain is assigned by the World Health Organization (WHO). As such, the INN name burlulipase initially refers exclusively to the lipolytically active protein as a pure active substance. In the real production of pharmaceutical active substances, however, this purest state represents a theoretical ideal, since the active substances, even though only in traces, still always contain accompanying substances and impurities. Thus, in addition to the active substance burlulipase (INN), the active ingredient burlulipase, too, inevitably contains accompanying substances and impurities. Therefore, in terms of the present invention, the term "burlulipase" is to be understood as meaning the different qualities of this active substance. In particular, during the production process, the active substance burlulipase is initially present in a quality, which still contains considerable quantities of the carbohydrate 6-deoxy-talane as an accompanying substance, a mixture of polymers and oligomers of 6-deoxy-talose (see Zahringer, U. et al., "Structure of a new 6-deoxy-α-D-talan from *Burkholderia* (*Pseudomonas*) *plantarii* strain DSM 6535, which is different from the O-chain of the lipopolysaccharide", Carbohydrate Research 300 (1997), 143-151.

Normally, 6-deoxy-talane is analytically detected in the form of its monomer 6-deoxy-talose. As a result of extensive separation of the 6-deoxy-talane, however, a very pure quality of the active substance burlulipase can also be obtained therefrom, which contains only small quantities of 6-deoxy-talane. In addition to 6-deoxy-talane, both qualities contain small amounts of other accompanying substances and impurities, including, in particular, rhamnolipids as lipopolysaccharides, but also, inter alia, rhamnose and lipids. Therefore, in terms of the present invention, the term "burlulipase" is to be understood as meaning all qualities of this active substance, in particular also the two qualities described above. The present invention relates to a preparation of burlulipase, which is an aqueous solution comprising burlulipase, which is characterized in that it contains calcium ions. Calcium ions have the property that they stabilize solutions of burlulipase in water against thermal stresses. Therefore, aqueous solutions containing burlulipase and calcium ions can be stored longer or at higher temperatures, without the activity loss being increased in comparison to a solution containing no calcium ions. Thereby, the expiration date is extended or the storage temperature can be increased. In that, aqueous solutions containing calcium chloride as described herein are preferred. In that, it is immaterial, whether the calcium chloride has been added as such or whether the calcium ions and chloride ions originate from different sources, as long as the solution contains calcium chloride, i.e. both calcium ions and chloride ions. Calcium chloride is a physiologically compatible form of calcium ions, which does not impair the effect of calcium ions on the burlulipase.

The present aqueous solutions as described herein preferably contain at least 10% by weight of water, more preferably at least 30% by weight of water and even more preferably at least 40% by weight of water, particularly preferably at least 50% by weight of water, and most preferably at least 70% by weight of water. It is also preferred that the aqueous solutions according to the invention contain less than 30% by weight, preferably less than 10% by weight, more preferably less than 5% by weight and most preferably less than 1% by weight of alcohols with a carbon number of 6 or less.

Normally, burlulipase is present in the solutions according to the invention in a mass concentration of 0.1 to 35 mg of protein/ml. Where the unit of a mass per volume, such as mg/ml, is used below for concentrations, these respectively are mass concentrations. For special applications, however, it is also possible to use mass concentrations outside this range. Preferably, the burlulipase is present in a concentration of 0.5 to 30 mg of protein/ml, more preferably in a concentration of 1 to 25 mg of protein/ml, and most preferably in a concentration of 3 to 20 mg of protein/ml. A concentration of 0.1 to 35 mg of protein/ml is easy to prepare and normally is physiologically active enough to be used in the treatment of a patient. A concentration of 0.5 to 30 mg of protein/ml is preferred, because at least a concentration of 0.5 mg of protein/ml is often necessary in order to achieve a sufficient dosage, and a concentration of 30 mg of protein/ml in a suitable formulation is stable even at room temperature over a period of at least 6 months. A concentration of 1 to 25 mg of protein/ml is sufficient for most therapies, and normally a concentration of 3 to 20 mg of protein/ml will be adequate. For use in pediatrics, concentrations of 2 to 10 mg of protein/ml are preferred.

In principle, the aqueous solution according to the invention as described herein can contain any amounts of calcium ions. Calcium ions exhibit a stabilizing effect even in very small quantities. The upper limit is essentially determined by the physiological compatibility of calcium ions. Normally, however, calcium ions are present in a concentration of up to 200 mmol/l, preferably in a concentration of 0.01 to 150 mmol/l. Where the unit of an amount of substance per volume, such as mmol/l, is used below for concentrations, these respectively are concentrations of substance amounts. In this amount, calcium ions are present in sufficient quantity to substantially stabilize all burlulipase molecules, but at the same time are not concentrated to such an extent that they lead to side effects. This in particular applies to the range from 0.1 to 50 mmol/l, which therefore is particularly preferred. High preference is given to an aqueous solution according to the invention as described herein, which contains calcium ions in an amount of 0.5 to 20 mmol/l. Most preferred, however, is an amount of 5 to 30 mmol. These small amounts additionally ensure that the physiologically tolerated amount of calcium chloride is not exceeded.

Particularly preferred is an aqueous solution according to the invention as described herein, which contains calcium chloride in the substance concentrations indicated above for calcium ions. The reasons for this are as described above for the use of calcium chloride and the amounts of calcium ions.

Aqueous solutions of burlulipase are normally most stable in a pH range from 4 to 9. Therefore, aqueous solutions according to the invention as described herein are preferred, which have a pH of 4 to 9. More preferred are such aqueous solutions according to the invention, which have a pH of 6 to 8, and particularly preferably of 7 to 8. The aqueous solutions according to the invention are most stable in a pH range from 7.3 to 7.7, and therefore such solutions according to the invention are most preferred, which have a pH of 7.3 to 7.7.

To adjust the pH value, acids and bases can be added to the aqueous solutions according to the invention as described herein in a simple manner. In that, the choice of acids and bases is not particularly limited. All possible acids and bases can be used for this purpose. Acids with a low pKa value, such as hydrochloric acid or sulfuric acid, and bases with a high pKa value, such as, for example, alkali hydroxides, are particularly suitable. pH buffers are also preferably used in order to adjust the pH appropriately. Such pH buffers ensure that the pH value is maintained permanently and prevent fluctuations in the acid and base contents of the raw materials used to prepare the solutions according to the invention from influencing the pH of the solutions according to the invention.

Preference is given to tris(hydroxymethyl)aminomethane for use as a constituent of the pH buffer in the aqueous solutions according to the invention. Therefore, an aqueous solution is preferred which contains tris(hydroxymethyl) aminomethane.

Furthermore, the aqueous solutions according to the invention can contain pharmaceutically acceptable excipients in customary amounts, which are known to the person skilled in the art from prior art. In particular, the aqueous solutions according to the invention can contain emulsifiers, solubilizers, flavors, odorants and colorants, solvents, sugars (glucose, lactose), preferably non-reducing sugars (trehalose, saccharose), alcohols, sugar alcohols (e.g., mannitol, sorbitol), lipids, amino acids, salts, electrolytes, antioxidants, preservatives and anti-microbially active substances. Other suitable excipients can be retrieved, for example, from the "Lexikon der Hilfsstoffe für Pharmazie, Kosmetik und angrenzende Gebiete" (Fiedler, Herbert P.; Vol. 2, 40 OVR Oberschwäbische Verlagsanstalt Ravensburg, 1989). The aqueous solution according to the invention can also contain carrier substances, wherein polyols and especially monosaccharides and polysaccharides are preferred. Particularly suitable excipients are listed, e.g., in the book "Pharmaceutical Formulation Development of Peptides and Proteins", Second Edition (CRC Press, authors: Lars Hovgaard, Sven Frokjaer, Marco van de Weer), in chapters 8 and 10, among others. Other suitable excipients as well as combinations thereof can be found in numerous publications and patent applications of Wolfgang Frieß, Gerhard Winter, John Carpenter, Michael Pikal, Patrick Garidel and Hanns-Christian Mahler.

As already described above, the aqueous solution according to the invention of a corresponding quality of the active substance burlulipase, as described herein, can contain considerable amounts of 6-deoxy-talane as an accompanying substance. In these cases, it particularly preferably contains 6-deoxy-talane in an amount of 1 to 60% by weight based on the dried active substance, and most preferably, in these cases, it contains 6-deoxy-talane in an amount of 15 to 40% by weight relative to the dried burlulipase. 6-deoxy-talane, however, also contributes to the thermal instability of burlulipase. Therefore, aqueous solutions according to the invention are preferred, in which 6-deoxy-talane is contained in an amount of 10% by weight or less, more preferably of 2% by weight or less, and particularly preferably of 1% by weight or less, respectively relative to burlulipase.

Furthermore, the aqueous solution according to the invention as described herein may contain impurities, which result from the preparation process. Burlulipase is normally obtained by expression from *Burkholderia plantarii*. Most of the impurities can be removed during the purification process. A small portion, however, can also be contained in the product after purification.

A further aspect of the present invention is a pharmaceutical product comprising an aqueous solution according to the invention as described herein. The major advantage of the aqueous solution according to the invention as described herein is that, compared to lipases obtained from animals, it does not have any viral or microbial impurities. In particular, it contains no viruses, bacteria or prions from animal sources and is therefore to be classified as harmless and free from side effects in this respect.

The pharmaceutical product according to the invention as described herein preferably is a pharmaceutical product for the treatment of exocrine pancreatic insufficiency. The effect of burlulipase in the treatment of exocrine pancreatic insufficiency is already known, and the pharmaceutical product according to the invention can substitute the pancreatin customarily used in this therapy. In that, the pharmaceutical product according to the invention has the advantage over pancreatin, that it contains no viral or microbial impurities. The pharmaceutical product according to the invention as described herein is particularly suitable for the treatment of pancreatic insufficiency in patients having mucoviscidosis.

Furthermore, the pharmaceutical product according to the invention as described herein is suitable for use in pediatrics. Pancreatin can only be provided as a solid and must be taken in large quantities, large dosage forms and/or in a large number of dosage forms (e.g., tablets or capsules) every day. This is often difficult, especially for children. The present aqueous solutions can be administered as beverages or in beverages accompanying meals, are therefore also easily accessible for children and also allow for high compliance in pediatrics.

Particularly preferably, the pharmaceutical product according to the invention as described herein is intended and suitable for use after sequential storage. In terms of this application, sequential storage shall mean that the pharmaceutical product is first stored in an uninterrupted cooling chain, but can also be kept at room temperature during the time immediately before as well as during the time after a package has been opened, until it has been used up. This is important in order to ensure an adequate supply of the patients with the active substance burlulipase. Without stabilization by calcium ions, the stability of burlulipase is limited. Even though an uninterrupted cooling chain is present at the manufacturer’s, in wholesale trade and in pharmacies, it is often difficult for the patient to ensure permanent cooling. Aside from the fact that many patients, especially in poorer countries, do not have any cooling options, it is often difficult for patients to apply the necessary discipline in order to ensure cooling. In particular while travelling or when being away from home all day, this frequently is a problem. This may lead to an undersupply of the patients. This in particular applies since the patient is not able to determine the remaining activity of the burlulipase.

The pharmaceutical product according to the invention, however, contains a stabilized form of the burlulipase, which makes it possible to also store the pharmaceutical product for a prolonged period outside a cooled location without the activity of the active ingredient decreasing below the activity required to be effective. Depending on the weather, the pharmaceutical product according to the invention can be stored at ambient temperature for up to four weeks or longer, without the activity decreasing too much. Depending on the climate zone, the size of the package can be adapted such that, with appropriate dosing, it is consumed before the activity of the lipase has decreased too much due to thermal deactivation. Therefore, the pharmaceutical product according to the invention can safely be carried along and taken by the patient him/herself, without the risk of incorrect dosing.

A further aspect of the present invention is an aqueous solution according to the invention as described herein or a pharmaceutical product according to the invention as described herein, wherein the solution or the pharmaceutical product is packaged in a container which has been produced by the blow-fill-seal process.

A further aspect of the present invention is also a process for producing a packaged aqueous solution as described herein or a packaged pharmaceutical product according to the invention as described herein, wherein the aqueous solution according to the invention or the pharmaceutical product according to the invention is packaged according to the blow-fill-seal process. In that, particular preference is given to a process as described herein comprising the steps of:

- providing a polymer
- extruding the polymer through an annular horizontal opening, so that a hanging tube is formed,
- cutting off the tube,
- closing the tube at the lower end,
- inserting the tube into a mold,
- inflating the tube, so that the tube fills the mold and the material of the tube forms the wall of a container,
- filling a solution according to the invention or a pharmaceutical product according to the invention into the container,
- closing the container, wherein at least the filling in of the solution or the pharmaceutical product, resp., and the closing of the container take place under sterile conditions. In that, the steps of cutting off the tube, closing the tube at the lower end and inserting the tube into a mold may be undertaken in any order. All other process steps are preferably carried out in the order stated. Particularly preferably all process steps are carried out in the order stated above.

Containers produced by the blow-fill-seal processes are plastic containers, which are opened by simply tearing them open or cutting them open or the like. Thus, in contrast to glass containers, the pharmaceutical product or the solution is available without great effort and can also be easily handled by laypersons, in particular patients. Thus, contrary to the use of vials, it is not necessary to handle needles and the like. Glass breakage also cannot occur. In comparison to glass bottles, these containers have the advantage that the pharmaceutical products are filled in in portions and permit accurate dosing. Containers produced by the blow-fill-seal processes are therefore ideally suited for administration of liquid pharmaceutical products for ingestion by the patients themselves. This in particular applies to indications in pediatrics.

EXAMPLES

Burlulipase was prepared according to Example 1 of EP 0 592 478 B2. This applies to all tests.

Example 1: Preliminary Studies for Stabilizing Burlulipase

In order to study the effect of various additives on the thermal stability of aqueous solutions of burlulipase, various solutions of burlulipase in water were measured by means of microcalorimetry. Microcalorimetry is an analytical method, in which the burlulipase (or another protein) is heated in the corresponding formulation. In that, the temperature at which the protein is unfolded is detected. It has been shown that a higher unfolding temperature is frequently accompanied by increased thermal stability of the protein. This in turn can require a longer runtime or a higher storage temperature. Details on this analytical method can be found in the article by Youssef and Winter mentioned above.

A dynamic differential calorimeter of the Nano DSC type of the company TA Instruments with their headquarters in New Castle (Del., USA) was used. Measurements took place with a temperature increase of 1 K/min. A solution of 2 mg/ml of burlulipase in water was prepared. Another solution containing 2 mg/ml of burlulipase and 10 mmol/l of calcium chloride in water was also prepared. The solutions contained no further constituents. Microcalorimetry measurement of the solution of burlulipase in water exhibited a peak at about 73° C. This shows that burlulipase unfolds in an aqueous solution at about 73° C. The corresponding curve for the calcium chloride-containing solution indicated an unfolding temperature of about 88° C., i.e. about 15° C. higher. This is a clear indication that calcium chloride could stabilize burlulipase.

Example 2: Measurement of the Lipolytic Activity of Aqueous Solutions of Burlulipase Aqueous solutions of burlulipase were prepared by dissolving the components in water. 4 solutions were prepared. The pH in all solutions was 7.5. Table 1 shows the compositions of the 4 solutions.

TABLE 1

| Ingredients | Solution 1 | Solution 2 | Solution 3 | Solution 4 |
| --- | --- | --- | --- | --- |
| Burlulipase [mg/ml] | 15 | 15 | 15 | 15 |
| Calcium chloride [mmol] | — | 1 | 10 | — |
| $NaH_2PO_4$ [mmol] | — | — | — | 5 |
| Water | Residue | Residue | Residue | Residue |

The 4 solutions were stored at four different temperatures for a period of several months under otherwise identical conditions. At specific intervals, the activity of the burlulipase was measured. The following tables reflect the results of the tests. All activities are given in percent of the lipolytic activity measured during preparation of the solutions.

TABLE 2

Temperature 2 to 8° C.

| Solution No. | Start | 3 months | 6 months | 9 months | 12 months | 15 months |
| --- | --- | --- | --- | --- | --- | --- |
| 1 | 100 | 107.7 | 102.7 | 108.7 | 96.8 | 107.6 |
| 2 | 100 | 107.7 | 105.4 | 104.1 | 100.6 | 114.8 |
| 3 | 100 | 111.4 | 109.1 | 113.2 | 108.7 | 109.1 |
| 4 | 100 | 104.2 | 97.4 | 96.0 | 95.8 | 104.7 |

TABLE 3

Temperature 25° C.

| Solution No. | Start | 3 months | 6 months | 9 months | 12 months |
| --- | --- | --- | --- | --- | --- |
| 1 | 100 | 94.8 | 84.6 | 85.9 | 81.3 |
| 2 | 100 | 109.4 | 102.8 | 101.7 | 79.5 |
| 3 | 100 | 113.1 | 106.4 | 110.0 | 107.7 |
| 4 | 100 | 92.2 | 83 | 80.2 | 76.1 |

TABLE 4

Temperature 30° C.

| Solution No. | Start | 3 months | 6 months | 9 months | 12 months |
| --- | --- | --- | --- | --- | --- |
| 1 | 100 | 95.1 | 83.2 | 82.6 | 82.2 |
| 2 | 100 | 113.6 | 99.6 | 105.4 | 102.0 |
| 3 | 100 | 120.0 | 102.5 | 112.7 | 110.4 |
| 4 | 100 | 104.3 | 85.1 | 86.8 | 82.5 |

TABLE 5

| | Temperature 40° C. | | | |
|---|---|---|---|---|
| Solution No. | Start | 3 months | 6 months | 9 months 12 months |
| 1 | 100 | 62.3 | 47.0 | not measured |
| 2 | 100 | 102.7 | 84.1 | not measured |
| 3 | 100 | 105.5 | 95.2 | not measured |
| 4 | 100 | 55.2 | 41.8 | not measured |

The data shows that calcium ions can stabilize the burlulipase. At a concentration of 10 mmol (solution 3), the effect is clearly more pronounced than at a concentration of 1 mmol (solution 4). Temperatures of 25 to 40° C. correspond to the temperatures to which uncooled medicinal substances are exposed. Therefore, the present invention makes it possible to produce liquid pharmaceutical products containing burlulipase. Compared to pharmaceutical products not stabilized with calcium ions, the pharmaceutical products according to the invention are stable enough to ensure a stable supply of the patients with burlulipase. On the other hand, phosphate seems to have a slightly destabilizing effect on burlulipase. In any case, the aqueous solutions according to the invention stabilized by calcium ions are suitable for sequential storage.

Example 3: Effect of 6-deoxy-talane

In this experiment, two burlulipases with different 6-deoxy-talane contents were compared. A depletion of the 6-deoxy-talane contained in the burlulipase can be achieved by size exclusion chromatography (SEC). Other methods are also known for this purpose.

The following table shows investigations on the thermal stability of aqueous solutions of burlulipase, which contain 15 mg/ml of burlulipase. In that, one type of burlulipase contains 30% by weight of 6-deoxy-talane in relation to the dried burlulipase and a second solution contains 1% by weight of 6-deoxy-talane in relation to the dried burlulipase. The pH of the solutions at the beginning of the measurements was 7.5. The measurements were carried out at two different temperatures (25° C. and 40° C.). In addition to the burlulipase, the solutions did not contain any other ingredients. The solutions were stored at two different temperatures for a period of 3 or 6 months, resp., under otherwise identical conditions. After 3 months and also after 6 months, if applicable, the activity of the burlulipase was measured. The following table shows the results of the experiments. All activities are given in percent of the lipolytic activity measured during preparation of the solutions.

TABLE 6

| Talane content | Temperature | Start | 3 months | 6 months |
|---|---|---|---|---|
| 30% by weight | 25° C. | 100 | 95.8 | 86.6 |
| 1% by weight | 25° C. | 100 | 103.5 | 94.6 |
| 30% by weight | 40° C. | 100 | 65.6 | — |
| 1% by weight | 40° C. | 100 | 79.9 | — |

As can be seen in the table, the burlulipase solution, which only contains 1% by weight of 6-deoxy-talane, is more stable than the comparative solution with 30% by weight. Therefore, using burlulipase with a low 6-deoxy-talane content in pharmaceutical products is appropriate.

The invention claimed is:

1. An active pharmaceutical grade lipase product, comprising:
   an aqueous shelf-stable, pharmaceutical grade solution comprising burlulipase stabilized by solubilized calcium ions, and at least one of 6-deoxy-talane, lipids, and rhamnolipids.

2. The active pharmaceutical grade lipase product according to claim 1, wherein the solution comprises calcium chloride.

3. The active pharmaceutical grade lipase product according to claim 1, wherein the concentration of burlulipase in the aqueous solution is 0.1 to 35 mg per ml.

4. The active pharmaceutical grade lipase product according to claim 3, wherein the concentration of burlulipase in the aqueous solution is 0.5 to 30 mg per ml.

5. The active pharmaceutical grade lipase product according to claim 4, wherein:
   the concentration of calcium ions in the aqueous solution is 0.1 to 200 mmol/l; or
   the solution comprises calcium chloride in a concentration of 0.1 to 200 mmol/l.

6. The active pharmaceutical grade lipase product according to claim 5, wherein the concentration of calcium ions or calcium chloride in the aqueous solution is 0.2 to 100 mmol/l.

7. The active pharmaceutical grade lipase product according to claim 6, wherein the concentration of calcium ions or calcium chloride in the aqueous solution is 0.5 to 50 mmol/l.

8. The active pharmaceutical grade lipase product according to claim 3, wherein the concentration of burlulipase in the aqueous solution is 1 to 25 mg per ml.

9. The active pharmaceutical grade lipase product according to claim 8, wherein:
   the concentration of calcium ions in the aqueous solution is 0.1 to 200 mmol/l; or
   the solution comprises calcium chloride in a concentration of 0.1 to 200 mmol/l.

10. The active pharmaceutical grade lipase product according to claim 9, wherein the concentration of calcium ions or calcium chloride in the aqueous solution is 0.2 to 100 mmol/l.

11. The active pharmaceutical grade lipase product according to claim 10, wherein the concentration of calcium ions or calcium chloride in the aqueous solution is 0.5 to 50 mmol/l.

12. The active pharmaceutical grade lipase product according to claim 3, wherein the concentration of burlulipase in the aqueous solution is 3 to 20 mg per ml.

13. The active pharmaceutical grade lipase product according to claim 12, wherein:
   the concentration of calcium ions in the aqueous solution is 0.1 to 200 mmol/l; or
   the solution comprises calcium chloride in a concentration of 0.1 to 200 mmol/l.

14. The active pharmaceutical grade lipase product according to claim 13, wherein the concentration of calcium ions or calcium chloride in the aqueous solution is 0.2 to 100 mmol/l.

15. The active pharmaceutical grade lipase product according to claim 14, wherein the concentration of calcium ions or calcium chloride in the aqueous solution is 0.5 to 50 mmol/l.

16. The active pharmaceutical grade lipase product according to claim 12, wherein the pH of the solution is 7.3 to 7.7.

17. The active pharmaceutical grade lipase product according to claim 1, wherein:
   the concentration of calcium ions in the aqueous solution is 0.1 to 200 mmol/l; or the solution comprises calcium chloride in a concentration of 0.1 to 200 mmol/l.

18. The active pharmaceutical grade lipase product according to claim 17, wherein the concentration of calcium ions or calcium chloride in the aqueous solution is 0.2 to 100 mmol/l.

19. The active pharmaceutical grade lipase product according to claim 18, wherein the concentration of calcium ions or calcium chloride in the aqueous solution is 0.5 to 50 mmol/l.

20. The active pharmaceutical grade lipase product according to claim 1, wherein the aqueous solution has a pH of 4 to 9.

21. The active pharmaceutical grade lipase product according to claim 20, wherein the pH of the solution is 6 to 8.

22. The active pharmaceutical grade lipase product according to claim 1, wherein the aqueous solution further comprises tris(hydroxymethyl)aminomethane.

23. The active pharmaceutical grade lipase product according to claim 1, wherein the solution is packaged in a container produced by a blow-fill-seal process.

24. The active pharmaceutical grade lipase product according to claim 1, wherein the aqueous solution further comprises one or more pharmaceutically acceptable excipients.

25. A product comprising:
a shelf-stable, pharmaceutical grade aqueous solution of burlulipase stabilized by solubilized calcium ions, and at least one of 6-deoxy-talane, lipids, and rhamnolipids.

26. The product of claim 25 wherein the aqueous solution is packaged in a container produced by a blow-fill-seal process.

* * * * *